United States Patent [19]

Quarderer et al.

[11] Patent Number: 5,093,541

[45] Date of Patent: *Mar. 3, 1992

[54] PREPARATION OF CYCLOBUTARENES VIA THE STEAM PYROLYSIS OF AROMATIC DERIVATIVES

[75] Inventors: George J. Quarderer; Mark J. Beitz; Fred C. Stone; Patrick M. O'Donnell, all of Midland, Mich.

[73] Assignee: The Dow Chemical Company, Midland, Mich.

[*] Notice: The portion of the term of this patent subsequent to Oct. 25, 2006 has been disclaimed.

[21] Appl. No.: 356,968

[22] Filed: May 25, 1989

Related U.S. Application Data

[63] Continuation-in-part of Ser. No. 111,895, Oct. 23, 1987, Pat. No. 4,851,603.

[51] Int. Cl.$^5$ .............................................. C07C 15/00
[52] U.S. Cl. ............................................... 585/410
[58] Field of Search ........................................... 585/410

[56] References Cited

U.S. PATENT DOCUMENTS 4,570,011  2/1986  Ying-Hung So ................ 560/8
4,540,763  9/1985  Kirchhoff ........................ 526/281
4,544,782  10/1985  Chapman et al. ............... 585/443

OTHER PUBLICATIONS

Klundt, *Chemical Reviews*, 70, pp. 471–487.

Boekelheide et al, *Tetrahedron Letters*, 44, pp. 4245–4248.
Boekelheide et al, *Topics in Current Chemistry*, 100, pp. 2892–2893.
Scheiss et al., *Tetrahedron Letters*, 46, pp. 4569–4572 (1978).
Scheiss et al., *Tetrahedron Letters*, vol. 23, No. 36, pp. 3265–3268 (1982).
Loudon et al., *J. of Am. Chem. Soc.*, 91:27, pp. 7577–7580 (1969).
Morello et al., *Tetrahedron Letters*, 46, pp. 4435–4436 (1979).
Maccoll et al., *J. C. S. Perkin II*, pp. 1194–1196 (1975).
Crow et al., *Aust. J. Chem.*, 28, pp. 1741–1754 (1975).
Harruff et al., *J. of Am. Chem. Soc.*, 100, pp. 2892–2894 (1978).
Berman et al., *J. of Am. Chem. Soc.*, 102, pp. 5692–5694 (1980).
Chapman et al., *J. of Am. Chem. Soc.*, 106, pp. 7974–7976 (1984).
Trahanovsky et al., *J. Org. Chem.*, 46, pp. 2985–2987 (1981).

*Primary Examiner*—Curtis R. Davis
*Attorney, Agent, or Firm*—Charles J. Enright

[57] ABSTRACT

Cyclobutarenes are prepared by pyrolyzing a suitable benzene, naphthalene, or pyridine derivative in the presence of an amount of steam effective to substantially reduce the partial pressure of the pyrolyzing compound.

6 Claims, No Drawings

PREPARATION OF CYCLOBUTARENES VIA THE STEAM PYROLYSIS OF AROMATIC DERIVATIVES

CROSS-REFERENCE TO RELATED APPLICATION

This is a continuation-in-part of copending U.S. application Ser. No. 111,895, filed Oct. 23, 1987 now U.S. Pat. No. 4,851,603.

BACKGROUND OF THE INVENTION

This invention relates to an improved process for preparing arylcyclobutenes, more commonly referred to as cyclobutarenes.

Cyclobutarenes, and in particular benzocyclobutene, are important intermediates for the preparation of monomeric and polymeric compositions. U.S. Pat. No. 4,540,763 discloses that biscyclobutarenes can be processed to prepare polymeric compositions. These compositions exhibit thermal stability at temperatures exceeding 250° C., chemical resistance to most conventional solvents, good mechanical and electrical properties, and low sensitivity to water. They are useful in advanced composites, adhesives, structural laminates, matrix resins, and planarization resins for the electronics and aerospace industries.

As disclosed in Schiess et al., *Tetrahedron Letters*, 46, pp 4569-4572 (1978), cyclobutarenes have been prepared by the flash vacuum pyrolysis of an orthomethylbenzylchloride derivative. For example, the flash vacuum pyrolysis of α-chloro-ortho-xylene (ACOX) will yield benzocyclobutene. The pyrolysis is performed under vacuum to achieve a low partial pressure of the reactant because the conversion of the reactant to the cyclobutarene prepared increases as the partial pressure of the reactant decreases.

The flash vacuum pyrolysis process has three main problems associated with it. First, expensive refrigeration equipment is required to condense the product and other expenses are required to operate under vacuum. Second, the process forms coke or tar on reactor internals and therefore prevents economical continuous operation. Third, hydrochloric acid, which is produced as a byproduct of the pyrolysis in some instances, is highly corrosive to the vacuum and refrigeration equipment.

Another method of decreasing the partial pressure of the reactant is disclosed in U.S. Pat. No. 4,570,011. This method uses a mixture of the reactant and an inert solvent, such as xylene, to decrease the concentration of the reactant during pyrolysis and therefore decrease its partial pressure. However, this method requires the use of a large quantity of solvent which must be separated from the cyclobutarene and recovered. More significantly, the operating pressure must still be reduced to a preferred pressure between 25 mm and 35 mm of mercury in order to achieve a desirable yield of the cyclobutarene.

In view of the deficiencies of the prior art, a process for preparing cyclobutarenes with acceptable yields at substantially atmospheric pressure is needed. Additionally, a process that sufficiently reduces coke or tar formation on reactor internals to allow continuous operation is needed. Furthermore, a process that aids in separating hydrochloric acid or any other acid produced during the reaction and does not require a large quantity of solvent would be highly desirable.

SUMMARY OF THE INVENTION

The present invention improves the known process of preparing a cyclobutarene by pyrolyzing a benzene or a naphthalene substituted with any of halomethyl, hydroxymethyl, acetoxymethyl or trifluoroacetoxymethyl and either methyl or substituted methyl ortho thereto having at least one hydrogen on the alpha carbon. The improvement comprises conducting the pyrolysis in the presence of an amount of steam effective to substantially reduce the partial pressure of the pyrolyzing compound.

In one embodiment hereof, the cyclobutarene product prepared in accordance with the subject invention has two or more cyclobutene rings fused to the benzene or naphthalene ring structure of the substituted aromatic starting material. In such embodiment the substituted aromatic starting material comprises two or more pairs of substituents which are capable of forming the indicated fused cyclobutene ring structure under pyrolysis conditions, each of said pairs of substituents comprising a first substituent selected from halomethyl, hydroxymethyl, acetoxymethyl and trifluoroacetoxymethyl and a second substituent which is located in the ortho position relative to said first substituent and which is selected from methyl or a substituted methyl group having at least one hydrogen on the alpha carbon.

Surprisingly, the steam does not hydrolyze the reactant during pyrolysis to reduce the yield of desired cyclobutarene, despite high pyrolysis temperatures. The steam functions as a diluent to reduce the reactant partial pressure so that vacuum operation is unnecessary. It also reduces coke or tar formation on reactor internals relative to the coke or tar formation exhibited during vacuum operation and allows economical continuous operation. When the steam condenses following the reaction, the aqueous phase formed contains the byproduct acid which can be easily separated from the cyclobutarene. The improvement provides a practical process for preparing cyclobutarenes at acceptable yields.

The cyclobutarenes prepared by the process of the present invention are necessary intermediates for the patented polymer compositions of U.S. Pat. No. 4,540,763 and for other thermally stable polymer compositions.

DETAILED DESCRIPTION OF THE INVENTION

The pyrolyzing compounds of this invention are known in the art. They are benzene or naphthalene compounds substituted with one or more substituent pairs, which substituent pairs individually comprises a first substituent selected from:

halomethyl ($-CH_2Cl$, $-CH_2Br$, $-CH_2F$),
hydroxymethyl ($-CH_2OH$), $$\text{acetoxymethyl } (-CH_2O\underset{\underset{O}{\|}}{C}-CH_3),$$

or $$\text{trifluoroacetoxymethyl } (-CH_2O\underset{\underset{O}{\|}}{C}-CF_3); \text{ and}$$

(a second substituent which is located ortho to said first substituent within the substituent pair in question and which is either methyl or substituted methyl The term "substituted methyl" refers to a substituent formed by replacing at least one hydrogen on methyl with any atom or radical, including but not limited to atoms or radicals such as halo, lower alkyl ($C_{1-4}$ alkyl), nitro, and cyano. The substituted methyl substituent must have at least one hydrogen on the alpha carbon.

The preferred halomethyl substituent is chloromethyl. The preferred substituted methyl substituents are lower alkyl, such as ethyl and propyl: and halomethyl. The most preferred substituted methyl substituent is chloromethyl.

The type of pyrolysis reaction necessary to prepare the cyclobutarenes of this invention depends on the particular pyrolyzing compound. If the pyrolyzing compound is substituted with halomethyl, then it undergoes dehydrohalogenation to form cyclobutarenes. Dehydrohalogenation is a reaction in which a hydrogen halide, such as hydrogen chloride or hydrogen bromide, is removed from the pyrolyzing compound. Dehydrohalogenation is illustrated as follows:

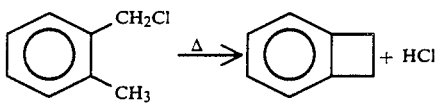

If the pyrolyzing compound is substituted with hydroxymethyl, then it undergoes dehydration to form cyclobutarenes. Similarly, if the pyrolyzing compound is substituted with acetoxymethyl or trifluoroacetoxymethyl, then it undergoes dehydrocarboxylation. Dehydrocarboxylation is a reaction in which a carboxylic acid, such as acetic acid or trifluoroacetic acid, is removed from the pyrolyzing compound. Dehydrocarboxylation is illustrated as follows:

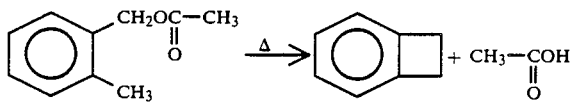

For purposes of describing this invention, a cyclobutarene is a benzene or naphthalene compound to which is fused one or more cyclobutane rings or one or more substituted cyclobutane rings. If a cyclobutane ring is substituted, then the preferred substituents are chloro or cyano.

U.S. Pat. No. 4,570,011; Scheiss et al., *Tetrahedron Letters*, 46, pp. 4569-72, (1978); and Scheiss et al., *Tetrahedron Letters*, Vol. 23, No. 36, pp. 3365-68, (1982): disclose substituted benzene and naphthalene compounds of this invention that can undergo dehydrohalogenation, dehydration, or dehydrocarboxylation to form cyclobutarenes.

The references disclose that the aromatic ring can be further substituted with at least one substituent stable to the pyrolysis conditions, including but not limited to substituents such as methyl, methoxy, methoxycarbonyl, nitro, chloro, bromo, and iodo. The most preferred pyrolyzing compound is ACOX, which when pyrolyzed will yield benzocyclobutene. Other preferred pyrolyzing compounds are represented by the following formula:

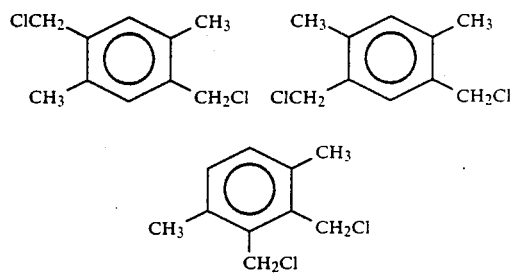

When these compounds are pyrolyzed, they will yield benzodicyclobutene. Benzodicyclobutene can be represented by either one of the following formulas:

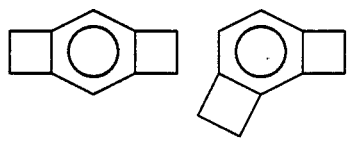

The pyrolyzing compounds of this invention can be prepared in situ from readily available raw materials. For example, ortho-xylene (o-xylene) can react with chlorine in situ to form ACOX, which can further react when pyrolyzed to form benzocyclobutene.

The reaction conditions that define this improved process are the mole ratio of steam to reactant (the reactant is the pyrolyzing compound of this invention), the reactor temperature and pressure, and the liquid hourly space velocity of the reactant through the pyrolysis reactor. The reaction conditions should be adjusted to achieve the highest possible conversion of reactant to desired product without excessive reactor volume and to reduce the formation of tar or coke in the reactor during the pyrolysis.

The mole ratio of steam to reactant in preferred embodiments ranges from about 5:1 to about 100:1, with a more preferred range from about 10:1 to about 40:1. If the ratio falls below about 5:1, then the conversion becomes unacceptable because of the increase in reactant partial pressure. If the ratio exceeds about 100:1, then the reactor volume becomes excessive and the cost of producing steam and disposing of condensate become burdensome.

The reactor temperature is similar to the temperature required for flash vacuum pyrolysis. It can range from about 400° C. to about 800° C., with a preferred range from about 550° C. to about 700° C. Temperatures below 400° C. require excessive reactor volume while temperatures above 800° C. enhance the likelihood of coke or tar formation. The reactor pressure can range from about 0.1 atmosphere to substantially atmospheric. Subatmospheric pressures are advantageous since conversion increases with a further reduction in reactant partial pressure. However, reactor pressures below about 0.1 atmosphere would require refrigeration equipment to condense the reactor effluent and are thus less attractive. Substantially atmospheric pressure is most convenient. Higher pressures can be employed, but would cause an undesirable increase in reactant partial pressure.

The liquid hourly space velocity is selected empirically based on the process conditions described above to maximize the conversion of reactant to desired product. In preferred embodiments it ranges from about 0.5 volume of liquid per volume of reactor per hour (v/v/hr) to about 10 v/v/hr. The more preferred range is from about 0.8 v/v/hr to about 3.0 v/v/hr.

The pyrolysis reaction can occur in a reactor of any shape or form that can tolerate temperatures exceeding at least 400° C. for the required reaction time. The preferred reactor configuration has a minimum of reactor internals upon which tar or coke can form and allows the residence time distribution to approach plug flow. One configuration that embodies these characteristics is a tubular reactor with a length to diameter ratio as great as practically possible. The preferred tubular reactor has a length to diameter ratio greater than 10:1.

The reactant and the steam can be fed to the reactor in any manner. They can be fed through different entry ports, or if desired, they can be premixed before entering the reactor. Preferably, the reactant is vaporized and combined with the steam before entering the reactor. The combined flowrate should remain as constant as possible to approach plug flow. Alternatively, water instead of steam can be fed to the reactor and subsequently vaporized in the reactor.

In a preferred embodiment of this invention, a uniform temperature is maintained within the reactor during pyrolysis. The elimination of localized "hot spots" reduces the formation of coke and tar on reactor internals and prevents the occurrence of secondary reactions. One method of maintaining a uniform temperature is to position the reactor in a fluidized bed of fine powder, such as alumina, silica, or magnesia, and then apply the necessary heat to the fluidized bed. The fluidized bed distributes the heat and prevents significant fluctuations in reactor temperature.

In another embodiment of this invention, the reactant is vaporized and preheated with the steam to near reaction temperature in a preheater before entering the reactor. The preheater configuration should effect sufficient mixing between the vaporized reactant and the steam to provide a uniform composition before entering the reactor.

Following the reaction, the products are condensed and form an organic phase and a wastewater phase. The products can be condensed in a conventional shell-and-tube heat exchanger. The organic phase generally contains the desired cyclobutarene and the wastewater phase contains water and possibly either the byproduct hydrogen halide or carboxylic acid, both of which would have been substantially diluted in water. The two phases can easily be separated by decantation.

In a preferred embodiment, condensed reactor effluent contacts the vaporized reactor effluent to quickly condense and cool the vaporized reactor effuent before it enters the heat exchanger. Rapid condensation and cooling of the reactor effuent reduces the formation of secondary products.

The improved process of this invention enables the skilled artisan to prepare cyclobutarenes with acceptable yields at atmospheric pressure. An acceptable yield of cyclobutarene is greater than about 20 weight percent. "Yield" is defined as the percent of reactant fed to the reactor that is converted to the desired cyclobutarene. The cyclobutarenes of this improved process are necessary intermediates for patented polymeric compositions prepared from biscyclobutarenes and other thermally stable polymer compositions.

The following examples are illustrative only and do not limit the scope of this invention.

EXAMPLE 1

A pyrolysis reactor is fabricated from a quartz tube having an inside diameter of 12 millimeters (mm) and a length of 53 centimeters (cm). The reactor is placed in an electric furnace and is heated to an average temperature of 606° C. 1.915 Grams per minute (g/min) of liquid ACOX at ambient temperature, 9.354 g/min of superheated steam at substantially atmospheric pressure, and 62 standard cubic centimeters per minute (SCCM) of nitrogen are fed cocurrently through different entry ports into the top of the reactor. The reaction mixture flows downward through the tubular reactor and the vaporized effluent exits at the bottom of the reactor. The reactor is maintained at substantially atmospheric pressure. The reactor effluent is condensed and cooled with water in a shell-and-tube heat exchanger and is allowed to decant in a product receiver. When a sufficient quantity of collected effluent is available, it is pumped out of the product receiver and is contacted with the vaporized reactor effluent to quickly condense and cool the effluent before it enters the heat exchanger.

After 144 minutes at these process conditions, the feeds are stopped. The collected effluent forms an organic phase and a wastewater phase in the product receiver. 139 Grams of the organic phase is separated from the wastewater phase in a separatory funnel. The organic phase is analyzed by gas chromatography using para-bromotoluene as an internal standard. The analysis shows that 46.5 percent of the ACOX reacted and that 45.0 percent of the ACOX that reacted formed benzocyclobutene. Therefore, the yield of ACOX to benzocyclobutene is 20.9 percent.

EXAMPLE 2

A tubular reactor is fabricated from coiled quartz tubing having an inside diameter of 15 mm and a length of 600 cm. The reactor is positioned in a fluidized bed of alumina powder. An electric furnace is used to heat the fluidized bed and to maintain the reactor temperature at 641° C.

37.1 Grams/min of liquid ACOX at ambient temperature, 91.3 g/min of low pressure steam superheated to 180° C., and 50 cm$^3$/min of nitrogen at 20° C. and 0.98 atm are initially fed cocurrently through different entry ports into the top of a quartz preheater. The quartz preheater is packed with 0.25 inch ceramic Intalox saddles and is heated to 550° C. in an electric furnace.

After the feeds are heated and vaporized in the preheater, they are fed into the top of the reactor. The reactor is maintained at substantially atmospheric pressure and the calculated average partial pressure of ACOX fed to the reactor is 37.6 mm mercury. The feeds pass through the coiled reactor. The reactor effluent is condensed and cooled in a shell-and-tube heat exchanger. The condensed effluent is collected in a product receiver.

After 32.3 hours, the feeds to the preheater are stopped. The collected effluent forms an organic layer and a wastewater layer in the product receiver. The organic layer s separated by decantation and analyzed by gas chromatography. The analysis shows that 45.4 percent of the ACOX reacted and that 65.6 percent of the ACOX that reacted formed benzocyclobutene. Therefore, the yield of ACOX to benzocyclobutene is 29.8 percent based on the recovered organic layer.

EXAMPLE 3

10.1 Grams per minute of liquid o-xylene at ambient temperature, 95 g/min of low pressure steam superheated to 180° C., 6.5 g/min of chlorine gas at ambient temperature, and 50 cm³/min of nitrogen at 20° C. and 0.98 atm are initally fed cocurrently through different entry ports into the top of the quartz preheater of Example 2. The quartz preheater is heated to 550° C.

After the feeds are heated and vaporized in the preheater, they are fed to the top of the fluidized bed reactor of Example 2. The reactor is maintained at substantially atmospheric pressure and at a temperature between 652° C. and 662° C. The calculated average partial pressures of o-xylene and chlorine are 13 mm and 25 mm mercury, respectively. The feeds pass through the coiled reactor. The reactor effluent is condensed and cooled in a shell-and-tube heat exchanger. The condensed effluent is collected in a product receiver.

After 50 minutes, the feeds to the preheater are stopped. The collected effluent forms an organic layer and a wastewater layer in the product receiver. The organic layer is separated by decantation and analyzed by gas chromatography, mass spectroscopy (GC/MS) and Fourier transform infrared spectroscopy (GC/FTIR). The analysis is as follows:

| Compound | GC Area (Percent) |
| --- | --- |
| o-xylene | 46.1 |
| ACOX | 23.9 |
| benzocyclobutene | 10.2 |
| other | 19.8 |

The analysis shows that o-xylene can react with chlorine in situ to form ACOX, and that ACOX can further react to form benzocyclobutene.

Upon repeating the procedures of this example and Examples 1 and 2 with other benzenes and naphthalenes, similar excellent results are obtained.

What is claimed is:

1. An improved process of preparing a cyclobutarene by pyrolyzing a substituted benzene or naphthalene starting material comprising two or more substituent pairs each of which individually comprises a first substituent selected from halomethyl, hydroxymethyl, acetoxymethyl, or trifluoroacetoxymethyl and a second substituent which is either methyl or a substituted methyl group having at least one hydrogen on the alpha carbon and which is located in the ortho position relative to said first substituent; wherein the improvement comprises conducting the pyrolysis in the presence of an amount of steam effective to substantially reduce the partial pressure of the pyrolyzing compound.

2. The process of claim 1 wherein the first substituents are halomethyl.

3. The process of claim 2 wherein the second substituents are lower alkyl or halomethyl.

4. The process of claim 1 wherein the cyclobutarene prepared is benzodicyclobutene and the pyrolyzing compound is represented by any one of the formulas:

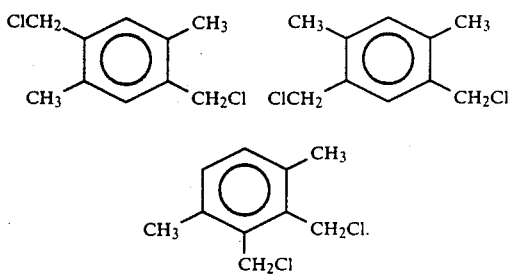

5. The process of claim 1 wherein the mole ratio of steam to pyrolyzing compound ranges from about 10:1 to about 40:1.

6. The process of claim 1 wherein the total reaction pressure is substantially atmospheric.

* * * * *